US012708604B2

(12) United States Patent
Wang et al.

(10) Patent No.: US 12,708,604 B2
(45) Date of Patent: Aug. 18, 2026

(54) LYOPHILIZED PREPARATION OF PROSTAGLANDIN E1 METHYL ESTER FOR INJECTION AND PRODUCTION AND USE THEREOF

(71) Applicant: Xi'an Hanfeng Pharmaceutical Co., Ltd., Xi'an City (CN)

(72) Inventors: Rutao Wang, Xi'an (CN); Long An, Xi'an (CN); Yi Zhao, Xi'an (CN); Jinghua Pang, Xi'an (CN); Tao Chen, Xi'an (CN)

(73) Assignee: Xi'an Hanfeng Pharmaceutical Co., Ltd., Xi'an City (CN)

( * ) Notice: Subject to any disclaimer, the term of this patent is extended or adjusted under 35 U.S.C. 154(b) by 1070 days.

(21) Appl. No.: 17/297,148

(22) PCT Filed: Oct. 28, 2019

(86) PCT No.: PCT/CN2019/113557

§ 371 (c)(1),
(2) Date: May 26, 2021

(87) PCT Pub. No.: WO2020/108193

PCT Pub. Date: Jun. 4, 2020

(65) Prior Publication Data

US 2022/0023219 A1 Jan. 27, 2022

(30) Foreign Application Priority Data

Nov. 27, 2018 (CN) ......................... 201811423561.7

(51) Int. Cl.

| | |
|---|---|
| ***A61K 9/19*** | (2006.01) |
| ***A61K 9/00*** | (2006.01) |
| ***A61K 31/5575*** | (2006.01) |
| ***A61K 47/10*** | (2017.01) |
| ***A61K 47/12*** | (2006.01) |
| ***A61K 47/24*** | (2006.01) |
| ***A61K 47/26*** | (2006.01) |
| ***A61K 47/44*** | (2017.01) |

(52) U.S. Cl.

CPC .............. *A61K 9/19* (2013.01); *A61K 9/0019* (2013.01); *A61K 31/5575* (2013.01); *A61K 47/10* (2013.01); *A61K 47/12* (2013.01); *A61K 47/24* (2013.01); *A61K 47/26* (2013.01); *A61K 47/44* (2013.01)

(58) Field of Classification Search

CPC .... A61K 9/19; A61K 9/0019; A61K 31/5575; A61K 47/10; A61K 47/12; A61K 47/24; A61K 47/26; A61K 47/44; A61K 9/1075; A61K 47/14; A61K 9/107; A61P 7/02; A61P 9/08; A61P 9/10; A61P 9/14

USPC .......................................................... 514/573

See application file for complete search history.

(56) References Cited

U.S. PATENT DOCUMENTS

| | | | | | |
|---|---|---|---|---|---|
| 4,849,451 | A * | 7/1989 | Mizushima | .......... | A61K 9/1075 514/530 |
| 5,635,491 | A * | 6/1997 | Seki | .................... | A61K 9/1075 514/53 |
| 5,681,850 | A | 10/1997 | Froelich | | |
| 5,741,523 | A | 4/1998 | Teagarden et al. | | |
| 5,977,172 | A * | 11/1999 | Yoshikawa | .......... | A61K 9/1075 514/530 |
| 6,673,841 | B2 | 1/2004 | Lee | | |
| 2015/0209516 | A1 | 7/2015 | Harkins, Jr. | | |
| 2017/0128362 | A1 | 5/2017 | Deng et al. | | |

FOREIGN PATENT DOCUMENTS

| | | | | | |
|---|---|---|---|---|---|
| CN | 1195990 | A | * 10/1998 | ........... | A61K 31/557 |
| CN | 1562041 | A | 1/2005 | | |
| CN | 101829054 | A | * 9/2010 | | |
| CN | 101843594 | B | 9/2010 | | |
| CN | 102000025 | A | 4/2011 | | |
| CN | 103637985 | A | 3/2014 | | |
| CN | 103655487 | A | * 3/2014 | | |
| CN | 103961356 | A | 8/2014 | | |
| CN | 105832744 | A | 8/2016 | | |
| CN | 105919949 | A | 9/2016 | | |
| CN | 106176600 | A | * 12/2016 | | |
| CN | 104706591 | B | * 9/2018 | ........... | A61K 31/557 |
| CN | 109394704 | A | 3/2019 | | |

(Continued)

OTHER PUBLICATIONS

AR do Vale Morais, 2016, International Journal of Pharmaceutics, 503 (2016) 102-114, http://dx.doi.org/10.1016/j.ijpharm.2016.02.047, Freeze-drying of emulsified systems: A review (Year: 2016).*

(Continued)

*Primary Examiner* — Jared Barsky

*Assistant Examiner* — Liyuan Mou

(74) *Attorney, Agent, or Firm* — Hoffman Warnick LLC

(57) ABSTRACT

The disclosure provides a lyophilized preparation of prostaglandin E1 methyl ester for injection and production and use thereof. The lyophilized preparation comprises the following components by weight: 0.1-10 parts of prostaglandin E1 methyl ester, 500-4000 parts of an oil for injection, 500-2000 parts of an emulsifier, 0-10 parts of a co-emulsifier, 5000-50000 parts of a lyoprotectant, and 200-1500 parts of glycerin. The prostaglandin E1 methyl ester lyophilized agent of the disclosure has less blood vessel irritation, good drug stability, and superior drug activity and therapeutic effect than similar prostaglandin E1 products.

3 Claims, 2 Drawing Sheets

(56) References Cited

FOREIGN PATENT DOCUMENTS

| | | | | |
|---|---|---|---|---|
| JP | 59216820 A | 12/1984 | | |
| JP | H05294924 A | 11/1993 | | |
| JP | 2006117704 A | 5/2006 | | |
| WO | WO-9709986 A1 * | 3/1997 | | ........... A61K 31/557 |
| WO | 03092617 A2 | 11/2003 | | |

OTHER PUBLICATIONS

First Office Action issued for corresponding Japanese Patent Application 2021-529847 mailed on Jun. 21, 2022, 7 pages.
Extended European Search Report issued on Jul. 1, 2022 for counterpart European patent application No. 19890056.5, 7 pages.
First Office Action and Search Report issued on Jul. 23. 2020 for counterpart Chinese patent application No. 201811423561.7, along with machine EN translation downloaded from EPO.
Second Office Action and Search Report issued on Mar. 10. 2021 for counterpart Chinese patent application No. 201811423561.7, along with machine EN translation downloaded from EPO.
Xiao Xu-ling et al., A Biogenetic Synthesis of Prostaglandin E1 Methyl Ester, Acta Pharmaceutica Sinica 1986.
Pharmaceutics, Pharmacy Teaching and Research Group of Nanjing University of Pharmacy, 1961.
Hu Rong-feng, Industrial Pharmacy, 2010.
PCT International Search Report for International Application No. PCT/CN2019/113557, dated Jan. 31, 2020, 3 pages.

* cited by examiner

PGE$_1$ $EC_{50}$ =9.767 nM

Compound of Example $EC_{50}$ =1.090 nM

LYOPHILIZED PREPARATION OF PROSTAGLANDIN E1 METHYL ESTER FOR INJECTION AND PRODUCTION AND USE THEREOF

CROSS-REFERENCE TO RELATED APPLICATIONS

This application is a National Stage of International Application No. PCT/CN2019/113557, filed Oct. 28, 2019, which claims priority to Chinese Patent Application No. 201811423561.7, filed Nov. 27, 2018, both of which are hereby incorporated by reference in their entireties.

TECHNICAL FIELD

The disclosure relates to the field of medicine. Specifically, the disclosure relates to a lyophilized preparation of prostaglandin E1 methyl ester for injection and production and use thereof.

BACKGROUND OF ART

Prostaglandin E1 (PGE1) is a natural endogenous vasodilator, which can be synthesized by human cells. It is an important substance that regulates cell function. It does not accumulate in the body, does not produce tolerance, and it's non-toxic without damaging side effects. It has a definite therapeutic effect and is superior to exogenous drugs. PGE1 has extremely strong physiological activity and a wide range of pharmacological activities. It can be used clinically in cardiovascular and cerebrovascular diseases, diabetic complications, respiratory diseases, pulmonary hypertension, hepatorenal syndrome (HRS), liver failure, nephropathy, etc. Studies have found that prostaglandin E1 not only has the effects of dilating blood vessels and reducing heart load, but also has the effects of excreting sodium, diuresis, strengthening the heart, improving coronary circulation, protecting myocardium, improving microcirculation and the like.

However, the common prostaglandin E1 fat emulsion injections currently on the market also have several obvious shortcomings: poor chemical stability, decreased content of prostaglandin E1 caused by high temperature sterilization, significantly increased content of degradation product PGA1, harsh product storage conditions (0~5° C.), and short effective period of only 1 year. Because prostaglandin E1 itself is an inflammatory substance, it has a strong pain when clinically applied to the human body, causing phlebitis, and limiting the product promotion.

In response to the above shortcomings, Chongqing Yaopharma developed a lyophilized emulsion of prostaglandin E1 (ZL201010168597.2)-Udil. The marketed product avoids the content loss caused by high temperature sterilization through sterilization by filtration, and overcomes the shortcoming of poor stability of prostaglandin E1 in aqueous preparations, and prolongs the effective period. However, cyclodextrin is used as a lyoprotectant in its formulation. Because there is a certain safety risk when cyclodextrin is used as an excipient for injection, especially the administration of β-cyclodextrin by injection can cause obvious nephrotoxicity, hemolysis, and necrosis at the injection site. The safety hazard of the preparation is significant, and the problem of injection pain is not solved (Instructions of Udil).

Prostaglandin E1 alkyl esters are currently considered to be prodrugs of prostaglandin E1. For example, U.S. Pat. No. 5,681,850 discloses prostaglandin E1 alkyl esters (C1-4) for the treatment of impotence. It is believed that prostaglandin E1 alkyl esters can be better absorbed through the skin by enhancing lipid solubility, and subsequently decomposed into prostaglandin E1 by hydrolase to take effect, so it is a prodrug; U.S. Pat. No. 6,673,841 discloses a prostaglandin E1 alkyl ester (C1-5) external preparation, which contains prostaglandin E1 alkyl ester as a prodrug, an oily vehicle, a skin permeation enhancer and an anti-irritant agent.

However, the inventors have unexpectedly found in the research that prostaglandin E1 methyl ester itself has strong biological activity and has a good prospect of preparing medicines. A fat emulsion preparation of alprostadil methyl ester is disclosed in the U.S. Pat. No. 4,849,451. However, the fat emulsion of alprostadil methyl ester prepared by us according to the examples thereof during the research is found to contain a significant number of large-size (>5 μm) emulsion droplets and fail to meet the requirement of emulsion droplet size, when measured using a new method, light blockage method in the United States Pharmacopoeia for the determination of the size of the emulsion droplet (the original common dynamic light scattering method cannot accurately determine the number of large-size particles above 5 μm). Large emulsion droplets (>5 um) can block capillaries and cause embolism, which poses a significant safety risk. In the United States, there has been a medical accident that the injection of large particles of fat emulsion lead to the death of a patient. Investigations and studies have shown that it is caused by the presence of emulsion particles larger than 5 μm in the emulsion. Therefore, in 2004, the United States Pharmacopeia formulated the detection methods and standards for determining the large particle size of emulsions. In view of the shortcomings and deficiencies of existing products, the disclosure aims to provide a new type of prostaglandin E1 methyl ester product with good stability, low safety risk and better efficacy.

SUMMARY

An object of the disclosure is to provide a lyophilized preparation of prostaglandin E1 methyl ester for injection.

Another object of the disclosure is to provide a method for producing a lyophilized preparation of prostaglandin E1 methyl ester for injection.

A further object of the disclosure is to provide a lyophilized preparation of prostaglandin E1 methyl ester for injection prepared by the production method.

A still further object of the disclosure is to provide use of the lyophilized preparation of prostaglandin E1 methyl ester for injection.

To achieve the above objects, in one aspect, the disclosure provides a lyophilized preparation of prostaglandin E1 methyl ester for injection, wherein the lyophilized preparation comprises the following components by weight: 0.1-10 parts of prostaglandin E1 methyl ester, 500-4000 parts of an oil for injection, 500-2000 parts of an emulsifier, 0-10 parts of a co-emulsifier, 5000-50000 parts of a lyoprotectant, and 200-1500 parts of glycerin.

According to some specific embodiments of the disclosure, the oil for injection is selected from one or more of soybean oil, medium chain oil, olive oil, tea oil, corn oil or castor oil.

According to some specific embodiments of the disclosure, the emulsifier is selected from lecithin and/or soybean phospholipid.

According to some specific embodiments of the disclosure, the co-emulsifier is selected from one or more of oleic acid, palmitic acid, stearic acid, linolenic acid, linoleic acid and sodium oleate.

According to some specific embodiments of the disclosure, the lyoprotectant is selected from one or more of lactose, sucrose, trehalose, mannitol, glucose and maltose.

According to some specific embodiments of the disclosure, the lyophilized preparation comprises the following components by weight: 0.1-10 parts of prostaglandin E1 methyl ester, 500-4000 parts of the oil for injection, 500-1500 parts of the emulsifier, 0-10 parts of the co-emulsifier, 5000-20000 parts of the lyoprotectant, and 200-1500 parts of glycerin.

According to some specific embodiments of the disclosure, wherein the lyophilized preparation comprises the following components per 100 ml before lyophilization: 0.1-10 mg of prostaglandin E1 methyl ester, 0.5-4 g of soybean oil, 0.5-1.5 g of lecithin, 0-0.01 g of sodium oleate, 5-20 g of lactose, and 0.2-1.5 g of glycerin.

It can be understood that the "per 100 ml" in "the lyophilized preparation comprises the following components per 100 ml before lyophilization" in the disclosure refers to every 100 ml of the prepared solution before lyophilization; that is, an aqueous solution containing each component.

According to some specific embodiments of the disclosure, the weight ratio of the lyoprotectant to prostaglandin E1 methyl ester is 20-500:0.01.

In another aspect, the disclosure further provides a method for producing a lyophilized preparation of prostaglandin E1 methyl ester for injection, wherein the method includes producing the lyophilized preparation with the following components as raw materials in weight percentage: 0.0001-0.01% of prostaglandin E1 methyl ester, 0.5-4% of the oil for injection, 0.5-2% of the emulsifier, 0-0.01% of the co-emulsifier, 5-50% of the lyoprotectant, 0.2-1.5% of glycerin, an appropriate amount of pH regulator, and a balance of water for injection.

According to some specific embodiments of the disclosure, the oil for injection is selected from one or more of soybean oil, medium chain oil, olive oil, tea oil, corn oil or castor oil.

According to some specific embodiments of the disclosure, the emulsifier is selected from lecithin and/or soybean phospholipid.

According to some specific embodiments of the disclosure, the co-emulsifier is selected from one or more of oleic acid, palmitic acid, stearic acid, linolenic acid, linoleic acid and sodium oleate.

According to some specific embodiments of the disclosure, the lyoprotectant is selected from one or more of lactose, sucrose, trehalose, mannitol, glucose and maltose.

According to some specific embodiments of the disclosure, the method includes producing the lyophilized preparation with the following components as raw materials in weight percentage: 0.0001-0.01% of prostaglandin E1 methyl ester, 0.5-4% of the oil for injection, 0.5-1.5% of the emulsifier, 0-0.01% of the co-emulsifier, 5-20% of the lyoprotectant, 0.2-1.5% of glycerin, an appropriate amount of pH regulator, and a balance of water for injection.

According to some specific embodiments of the disclosure, the method includes producing the lyophilized preparation with the following components as raw materials by weight: 0.1-10 parts of prostaglandin E1 methyl ester, 500-4000 parts of soybean oil, 500-1500 parts of lecithin, 0-10 parts of sodium oleate, 5000-20000 parts of lactose, 20-1500 parts of glycerin, an appropriate amount of sodium citrate or hydrochloric acid, and a balance of water for injection based on $100\times10^3$ parts of the total weight of raw materials.

According to some specific embodiments of the disclosure, the amount of the pH adjusting agent is such that the pH of the mixed solution is adjusted to 4.5-6.5 when the mixed solution is made up to the full volume with water for injection.

According to some specific embodiments of the disclosure, the method includes the following steps:

a. dispersing prostaglandin E1 methyl ester and ⅓ of the emulsifier uniformly in an oily solvent as an oil phase;
b. dissolving glycerin, the lyoprotectant, and the remaining emulsifier in an appropriate amount of water for injection as a water phase, and adjusting the pH of the water phase to 4.5-6.5 with a pH regulator;
c. dissolving the co-emulsifier in the oil or water phase;
d. adding the oil phase to the water phase under stirring, or adding the water phase to the oil phase under stirring, and obtaining an initial emulsion by shearing, then diluting to full volume with water for injection;
e. homogenizing the initial emulsion to obtain a uniform emulsion;
f. sterilizing the obtained emulstion by filtration, packing, lyophilizing and sealing to obtain the lyophilized preparation.

According to some specific embodiments of the disclosure, step d is to obtain the initial emulsion by shearing at a constant temperature of 20° C. to 50V.

According to some specific embodiments of the disclosure, the lyophilization process of step f includes pre-freezing at −50° C. to −35° C. for 100-200 minutes, and then vacuuming at 70-90 mTorr for 420-540 minutes at −25° C. to −15° C., then vacuuming at 50-70 mTorr for 240-360 minutes at 5° C. to 15° C., and then vacuuming at 35-45 mTorr for 300-420 minutes at 35° C. to 45° C.

According to some specific embodiments of the disclosure, the lyophilization process of step f includes pre-freezing at 40° C. for 150 minutes, and then vacuuming at 80 mTorr for 480 minutes at −20° C., then vacuuming at 60 mTorr for 300 minutes at 10° C., and then vacuuming at 40 mTorr for 360 minutes at 40° C.

In a further aspect, the disclosure also provides a lyophilized preparation of prostaglandin E1 methyl ester for injection prepared by the production method of the disclosure.

In a still further aspect, the disclosure also provides use of the lyophilized preparation of prostaglandin E1 methyl ester for injection in the preparation of a vasodilator.

According to some specific embodiments of the disclosure, the vasodilator is used to treat microcirculation disorders.

According to some specific embodiments of the disclosure, the microcirculation disorder is caused by thromboangiitis obliterans, arteriosclerosis obliterans, diabetes, frostbites, burns or bedsores.

The inventor has unexpectedly found in the research that prostaglandin E1 methyl ester itself has strong biological activity, and its anticoagulant and vasodilator activities are superior to those of prostaglandin E1, and it has a good potential for drug development. Through further formulation research, the inventor has chosen a lyophilized agent as the preparation form of prostaglandin E1 methyl ester, and unexpectedly found that the lyophilized preparation of prostaglandin E1 methyl ester prepared by the disclosure has the following remarkable features compared with existing preparations:

1. The lyophilized preparation of prostaglandin E1 methyl ester of the disclosure shows better drug activity and therapeutic effect than Udil in specific experimental examples.

2. Compared with the fat emulsion, the lyophilized preparation of prostaglandin E1 methyl ester of the disclosure significantly reduces the average particle size of the emulsion droplets and reduces the proportion of large-size emulsion droplets, which unexpectedly improves the pharmacokinetic behavior, thereby improving the drug effect.

3. It significantly reduces the free drug content after reconstitution of the lyophilized preparation, in particular, the free drug is not significantly increased when being diluted 10 times in accordance with the instructions of the administration method, avoiding the irritation of vascular injection.

4. It significantly improves the stability of the formulation, reduces the demand for production, transportation and storage conditions, and prolongs the effective period.

DETAILED DESCRIPTION

Figure 1:
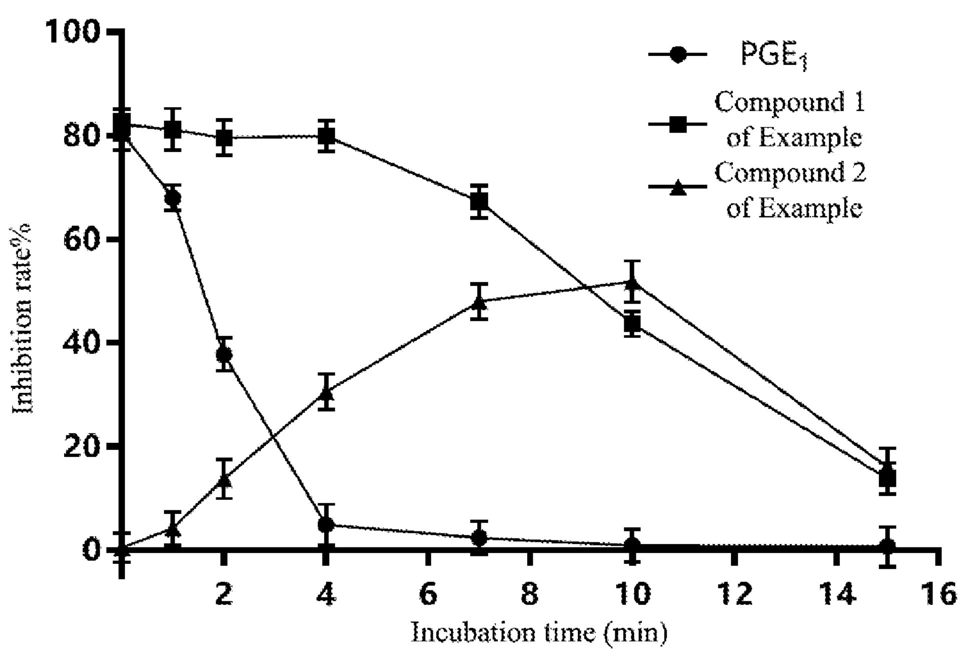
FIG. 1 is a curve showing the relationship between the inhibitory rate of the compound on ADP-induced platelet aggregation and the incubation time in Experimental Example 1.

The technical solutions of the disclosure will be described in detail below in conjunction with the drawings and examples, but the protection scope of the disclosure includes but is not limited to these.

Example 1

Synthesis of Compound 1 of the Disclosure (methyl [(1R,2R,3R)-3-hydroxy-2-(S,E)-3-hydroxyoct-1-enyl)-5-oxocyclopentyl]heptanoate) (prostaglandin E1 methyl ester

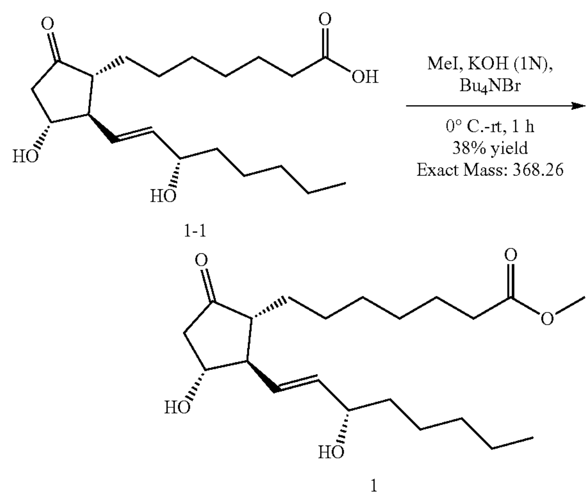

1-1

1

The starting material PGE1 (63 mg, 0.18 mmol) was added to a three-necked flask, and then a prepared 1M dry $THF/Et_2O$ solution was added and stirred to dissolve. Under ice bath conditions, MeI (26 mg, 1M) solution was slowly added dropwise to the reaction solution, and after the completion of dropwise addition, KOH (10 mg, 0.18 mmol) and $Bu_4NBr$ (6 mg, 0.018 mmol) were added. After the reaction solution was stirred for 1 h, it was heated to room temperature and monitored by TLC until the end of the reaction. The reaction was quenched by adding 20 ml of water. It was extracted with EtOAc (10 mL×3), and the organic phases were combined, dried over anhydrous $Na_2SO_4$ and filtered. The filtrate was concentrated under reduced pressure and purified by column chromatography (eluent n-hexane/EA=1/1) to obtain a white solid product (24.8 mg, 38% yield).

LCMS (MS Found: 391.3 $[M+Na]^+$).

$^1$HNMR (400 MHZ, DMSO) (ppm): 5.46 (s, 2H), 5.01 (s, 1H), 4.57 (s, 1H), 3.88 (s, 2H), 3.57 (s, 3H), 1.9-2.3 (m, 5H) 1.2-1.48 (m, 19H), 0.85 (s, 3H).

Example 2

Synthesis of Compound 2: (ethyl [(1R,2R,3R)-3-hydroxy-2-(S,E)-3-hydroxyoct-1-enyl)-5-oxocyclopentyl]heptanoate) (Prostaglandin E1 ethyl ester

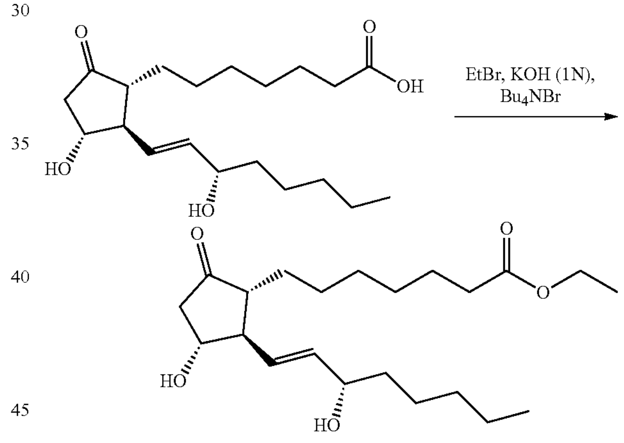

The starting material PGE1 (63 mg, 0.18 mmol) was added to a three-necked flask, and then a prepared 1M dry $THF/Et_2O$ solution was added and stirred to dissolve. Under ice bath conditions, EtBr (20 mg, 1M) solution was slowly added dropwise to the reaction solution, and after the completion of dropwise addition, KOH (10 mg, 0.18 mmol) and $Bu_4NBr$ (6 mg, 0.018 mmol) were added. After the reaction solution was stirred for 1 h, it was heated to room temperature and monitored by TLC until the end of the reaction. The reaction was quenched by adding 20 ml of water. It was extracted with EtOAc (10 mL×3), and the organic phases were combined, dried over anhydrous $Na_2SO_4$ and filtered. The filtrate was concentrated under reduced pressure and purified by column chromatography (eluent n-hexane/EA=1/1) to obtain a white solid product (20.5 mg, 29.8% yield).

LCMS (MS Found: 405 $[M+Na]^+$.

$^1$HNMR (400 MHZ, DMSO) (ppm): 5.46 (s, 2H), 5.01 (s, 1H), 4.57 (s, 1H), 3.88 (s, 2H), 3.57 (s, 3H), 1.9-2.3 (m, 7H) 1.2-1.48 (m, 19H), 0.85 (s, 3H).

Lyophilized Preparations of Prostaglandin E1 Methyl Ester with Different Main Drug Content Example 3

| Component | content |
|---|---|
| Prostaglandin E1 methyl ester | 0.5 mg |
| Soybean oil | 2 g |
| Lecithin | 1.5 g |
| Sodium oleate | 0.01 g |
| Lactose | 12.5 g |
| Glycerin | 0.75 g |
| Sodium citrate/hydrochloric acid | Appropriate amount |
| Water for Injection | Balanced to 100 mL |

The preparation process is as follows:

Oil phase: 2 g of soybean oil was weighted, 0.5 g of lecithin, and 0.5 mg of prostaglandin E1 methyl ester were added, and dissolved under shearing at 50° C.;

Water phase: 90 g of water for injection was weighted, 0.75 g of glycerin, 12.5 g of lactose, 0.01 g of sodium oleate were added, and mixed uniformly under shearing. The pH was adjusted to 6.5 with 0.1 M sodium citrate, then 1 g of lecithin was added, and continued shearing for 10 min.

The oil phase was slowly added to the water phase, continued shearing at 50° C. for 10 minutes to obtain an initial emulsion, and water was balanced to 100 mL;

The initial emulsion was passed through a homogenizer and homogenized 8 times at a pressure of 850 bar;

The homogenized emulsion was sterilized by filtration, packaged, pre-frozen at −40° C. for 150 minutes, vacuumed at 80 mTorr for 480 minutes at −20° C., vacuumed at 60 mTorr for 300 minutes at 10° C., vacuumed at 40 mTorr for 360 minutes at 40° C., and capped under vacuum to obtain the lyophilized powder for injection.

Example 4

| Component | content |
|---|---|
| Prostaglandin E1 methyl ester | 0.1 mg |
| Soybean oil | 2 g |
| Lecithin | 1.5 g |
| Sodium oleate | 0.01 g |
| Lactose | 5 g |
| Glycerin | 1.5 g |
| Sodium citrate/Hydrochloric acid | Appropriate amount |
| Water for Injection | Balanced to 100 mL |

The preparation process was the same as Example 3

Example 5

| Component | content |
|---|---|
| Prostaglandin E1 methyl ester | 10 mg |
| Soybean oil | 2 g |
| Lecithin | 1.5 g |
| Sodium oleate | 0.01 g |
| Lactose | 20 g |
| Glycerin | 0.5 g |
| Sodium citrate/Hydrochloric acid | Appropriate amount |
| Water for Injection | Balanced to 100 mL |

The preparation process was the same as Example 3

Lyophilized Preparations of Prostaglandin E1 Methyl Ester with Different Oils for Injection, Phospholipids and Contents Thereof Example 6

| Component | content |
|---|---|
| Prostaglandin E1 methyl ester | 0.5 mg |
| Olive oil | 0.5 g |
| Lecithin | 0.5 g |
| Sodium oleate | 0.005 g |
| Lactose | 12.5 g |
| Glycerin | 0.75 g |
| Sodium citrate/Hydrochloric acid | Appropriate amount |
| Water for Injection | Balanced to 100 mL |

The preparation process was the same as Example 3

Example 7

| Component | content |
|---|---|
| Prostaglandin E1 methyl ester | 0.5 mg |
| Soybean oil | 1 g |
| Lecithin | 0.8 g |
| Sodium Oleate | 0.01 g |
| Lactose | 12.5 g |
| Glycerin | 0.75 g |
| Sodium citrate/Hydrochloric acid | Appropriate amount |
| Water for Injection | Balanced to 100 mL |

The preparation process was the same as Example 3

Example 8

| Component | content |
|---|---|
| Prostaglandin E1 methyl ester | 0.5 mg |
| Soybean oil | 4 g |
| Soybean phospholipid | 2 g |
| Sodium Oleate | 0.01 g |
| Lactose | 12.5 g |
| Glycerin | 0.75 g |
| Sodium citrate/Hydrochloric acid | Appropriate amount |
| Water for Injection | Balanced to 100 mL |

The preparation process was the same as Example 3

Example 9

| Component | content |
|---|---|
| Prostaglandin E1 methyl ester | 0.5 mg |
| Tea oil | 2 g |
| Lecithin | 1.5 g |
| Sodium oleate | 0.01 g |
| Lactose | 12.5 g |
| Glycerin | 0.75 g |
| Sodium citrate/Hydrochloric acid | Appropriate amount |
| Water for Injection | Balanced to 100 mL |

The preparation process was the same as Example 3

Example 10

| Component | content |
|---|---|
| Prostaglandin E1 methyl ester | 0.5 mg |
| Corn oil | 2 g |
| Soybean phospholipid | 1 g |
| Sodium oleate | 0.01 g |
| Lactose | 12.5 g |
| Glycerin | 0.75 g |
| Sodium citrate/Hydrochloric acid | Appropriate amount |
| Water for Injection | Balanced to 100 mL |

The preparation process was the same as Example 3

Lyophilized Preparations of Prostaglandin E1 Methyl Ester with Different Co-Emulsifiers and Contents Thereof Example 11

| Component | content |
|---|---|
| Prostaglandin E1 methyl ester | 0.5 mg |
| Soybean oil | 2 g |
| Lecithin | 1.5 g |
| Oleic acid | 0.01 g |
| Lactose | 12.5 g |
| Glycerin | 0.75 g |
| Sodium citrate/Hydrochloric acid | Appropriate amount |
| Water for Injection | Balanced to 100 mL |

The preparation process was the same as Example 3

Example 12

| Component | content |
|---|---|
| Prostaglandin E1 methyl ester | 0.5 mg |
| Soybean oil | 2 g |
| Lecithin | 1.5 g |
| Stearic acid | 0.005 g |
| Lactose | 12.5 g |
| Glycerin | 0.75 g |
| Sodium citrate/Hydrochloric acid | Appropriate amount |
| Water for Injection | Balanced to 100 mL |

The preparation process was the same as Example 3

Example 13

| Component | content |
|---|---|
| Prostaglandin E1 methyl ester | 0.5 mg |
| Soybean oil | 2 g |
| Lecithin | 1.5 g |
| Linoleic acid | 0.01 g |
| Lactose | 12.5 g |
| Glycerin | 0.75 g |
| Sodium citrate/Hydrochloric acid | Appropriate amount |
| Water for Injection | Balanced to 100 mL |

The preparation process was the same as Example 3

Example 14

| Component | content |
|---|---|
| Prostaglandin E1 methyl ester | 0.5 mg |
| Soybean oil | 2 g |
| Lecithin | 1.5 g |
| Lactose | 12.5 g |
| Glycerin | 0.75 g |
| Sodium citrate/Hydrochloric acid | Appropriate amount |
| Water for Injection | Balanced to 100 mL |

The preparation process was the same as Example 3

Lyophilized Preparations of Prostaglandin E1 Methyl Ester with Different Lyoprotectants and Contents Thereof Example 15

| Component | content |
|---|---|
| Prostaglandin E1 methyl ester | 0.5 mg |
| Soybean oil | 2 g |
| Lecithin | 1.5 g |
| Sodium oleate | 0.01 g |
| Sucrose | 12.5 g |
| Glycerin | 0.75 g |
| Sodium citrate/Hydrochloric acid | Appropriate amount |
| Water for Injection | Balanced to 100 mL |

The preparation process was the same as Example 3

Example 16

| Component | content |
|---|---|
| Prostaglandin E1 methyl ester | 1 mg |
| Soybean oil | 2 g |
| Lecithin | 1.5 g |
| Sodium oleate | 0.01 g |
| Trehalose | 20 g |
| Glycerin | 0.5 g |
| Sodium citrate/Hydrochloric acid | Appropriate amount |
| Water for Injection | Balanced to 100 mL |

The preparation process was the same as Example 3

Example 17

| Component | content |
|---|---|
| Prostaglandin E1 methyl ester | 0.5 mg |
| Soybean oil | 2 g |
| Lecithin | 1.5 g |
| Sodium oleate | 0.01 g |
| Mannitol | 10 g |
| Glycerin | 0.75 g |
| Sodium citrate/Hydrochloric acid | Appropriate amount |
| Water for Injection | Balanced to 100 mL |

The preparation process was the same as Example 3

Example 18

| Component | content |
|---|---|
| Prostaglandin E1 methyl ester | 5 mg |
| Soybean oil | 2 g |
| lecithin | 1.5 g |
| Sodium oleate | 0.01 g |
| Lactose | 50 g |
| Glycerin | 0.2 g |
| Sodium citrate/Hydrochloric acid | Appropriate amount |
| Water for Injection | Balanced to 100 mL |

The preparation process was the same as Example 3

Comparative Example 1

It is prepared according to Example 2 in U.S. Pat. No. 4,849,451.

Comparative Example 2

The lyoprotectant used in the formulation of the disclosure (Example 3 of this disclosure) was added to the preparation obtained in Comparative Example 1 for lyophilization.

Experimental Example 1

The Effect in the Anti-Platelet Aggregation Test In Vitro

When healthy adult SD rats were anesthetized by intraperitoneal injection of 10% chloral hydrate, fresh whole blood was collected from the abdominal aorta and added to a centrifuge tube anticoagulated with 3.8% sodium citrate solution, and centrifuged at 900 rpm for 10 minutes to remove the upper platelet-rich plasma (PRP) for use. The tube having PRP removed was further centrifuged at 4000 rpm for 10 minutes, and the upper clarified plasma (PPP) was removed for use. In the experiment, Techlink model LBY-NJ4 4-channel platelet aggregator was used to determine the anticoagulant efficacy of each compound.

Into a sample cup containing 300 μL of PRP, 2 μL of 100 μM PGE1, Compound 1 of Example, Compound 2 of Example and methanol (solvent) were first added. After incubated for different periods (0, 1, 2, 4, 7, 10, 15 min), 204, of aggregation inducer 180 μM ADP solution was added. The aggregation rate of each sample was measured, and the inhibitory rate of the compound on ADP-induced platelet aggregation was calculated.

Inhibition rate %=(solvent aggregation rate−compound aggregation rate)/solvent aggregation rate×100%

From the results (shown in FIG. 1), it can be seen that the additions of PGE1 and Compound 1 of Example to PRP take effect immediately, and the inhibition rates were equivalent. With prolonged incubation time, the anticoagulant efficacy of the compound of the Example slowly decreased, and the inhibition rate is still 43.66% after 10 minutes, but the inhibition rate of PGE1 is only 4.93% after 4 minutes of incubation. Compound 2 of Example does not take effect immediately after the addition, and the efficacy gradually increased over time, and reaches the maximum inhibition rate of 51.86% after 10 minutes of incubation. Therefore, Compound 1 of Example is an active non-prodrug compound, and its anticoagulant effect is 2 times longer than that of PGE1, and Compound 2 of Example is a typical prodrug compound.

Experimental Example 2

Vasodilation Test In Vitro

In the experiment, rabbits were selected to prepare isolated aortic ring specimens: New Zealand white rabbits, male, weighing (2.5±0.3) kg. The rabbit was stunned with a blunt instrument, fixed on the rabbit dissecting table, and the thoracic aorta was quickly separated, and placed in a petri dish filled with saturated Kerbs solution (containing NaCl 6.9 g, KCl 0.35 g, $MgSO_4.7H_2O$ 0.29 g, $KH_2PO_4$ 0.16 g, $NaHCO_3$ 2.1 g, $CaCl_2$ 0.28 g, glucose 2 g per 1000 mL) at 37° C. and continuously introduced with mixed gas (95% $O_2$, 5% $CO_2$). The remaining blood in the blood vessel was squeezed out, and the peripheral fat and connective tissue were carefully peeled off, and it was cut into 0.5 cm long arterial rings for use. Two stainless steel L-shaped hooks were used to pierce through the vascular lumen of the vascular ring, and the vascular ring was hung horizontally in a 20 mL bath tube, fixed at the bottom, and connected to a tension transducer with a thin steel wire at the top. The resting tension was first adjusted to 0.00 g, and after stabilization for 20 minutes, 3.00 g tension was applied, and the tension level was continuously adjusted to maintain it at about 3.00 g and stabilized for 2 h (replacing the Kerbs solution along the wall of the bath every 15 minutes).

BL-420S biological function experiment system (Chengdu Techman Technology) was used to record the variation of vascular ring tension. After the vascular ring contraction was stable, prostaglandin E1 and the compounds of the Examples were accumulatively added to successively increase the final mass concentration of prostaglandin E1 in the bath tube to 0.05, 0.1, 0.2, 0.4, 0.8, 1.6, 3.2, 6.4, 12.8, 25.6 nM, and the diastolic efficacies of the vascular ring were recorded.

Figure 2:
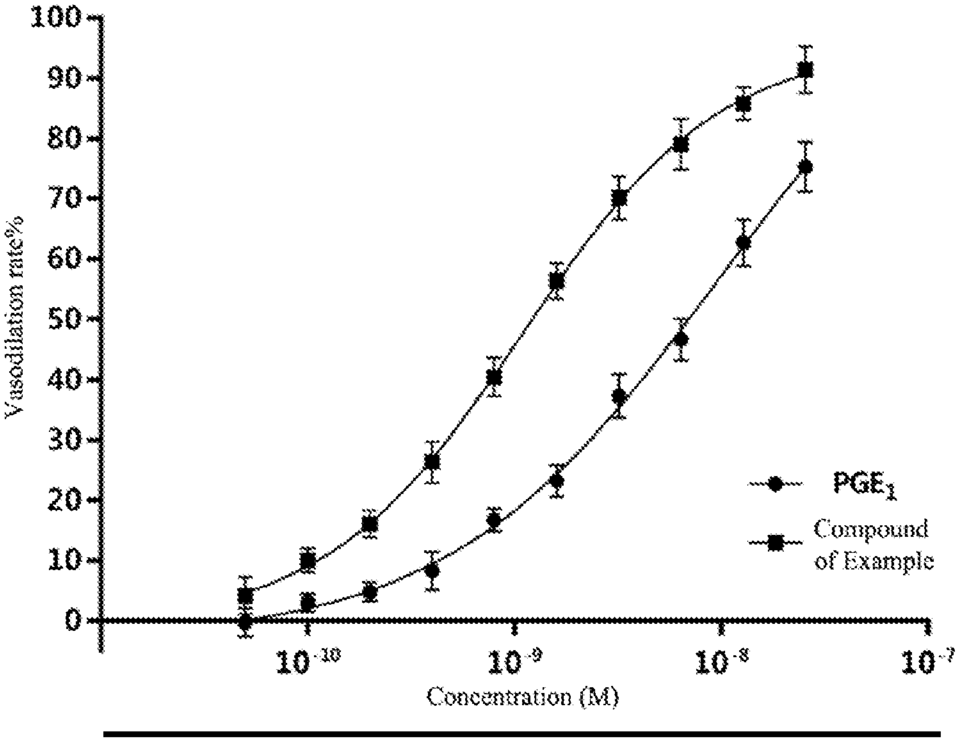
FIG. 2 is a curve showing the relationship between the diastolic efficacy of the vascular ring and the concentration of prostaglandin E1 in Experimental Example 2.

The results (shown in FIG. 2) show that under the experimental conditions, the diastolic efficacy of the compound of Example 1 on isolated rabbit blood vessels ($EC_{50}$=1.090 nM) is significantly stronger than that of PGE1 ($EC_{50}$=9.767 nM).

Experimental Example 3

Mesenteric Microcirculation Disorder Model

Rats were anesthetized with 2.5% sodium pentobarbital 30 mg/kg ip, fixed in the dorsal position, a 3 to 4 cm long incision was made in the midline of the abdomen, a section of small mesentery was gently pulled back to the cecum, and placed in an organic glass constant temperature water bath filled with physiological saline at 37° C. The mesentery was kept moist and laid flat on the organic convex observation table in the center of the bath, and pressed with a fixing plate. The video image under the microscope was collected by the camera of the biological microscope (magnification 40×), and the BI-2000 microcirculation observation system was used to real-time analyze the collected video images under the microscope.

A visual field was fixed and balanced for 10 minutes, and then the diameter and flow velocity of arterioles and venules in the selected area were observed. Then, 100 μL of a 1:100 diluted epinephrine hydrochloride physiological saline solution was added dropwise into the selected area, and an equal volume of physiological saline was added in the normal control group. At the same time, 10 μg/kg of the preparation of Example and Udil were immediately administered via the tail vein. The diameters of mesenteric arterioles were measured at 0.5, 1.2, 4, 6, 8, 10, 12, 15 min after administration.

Figure 3:
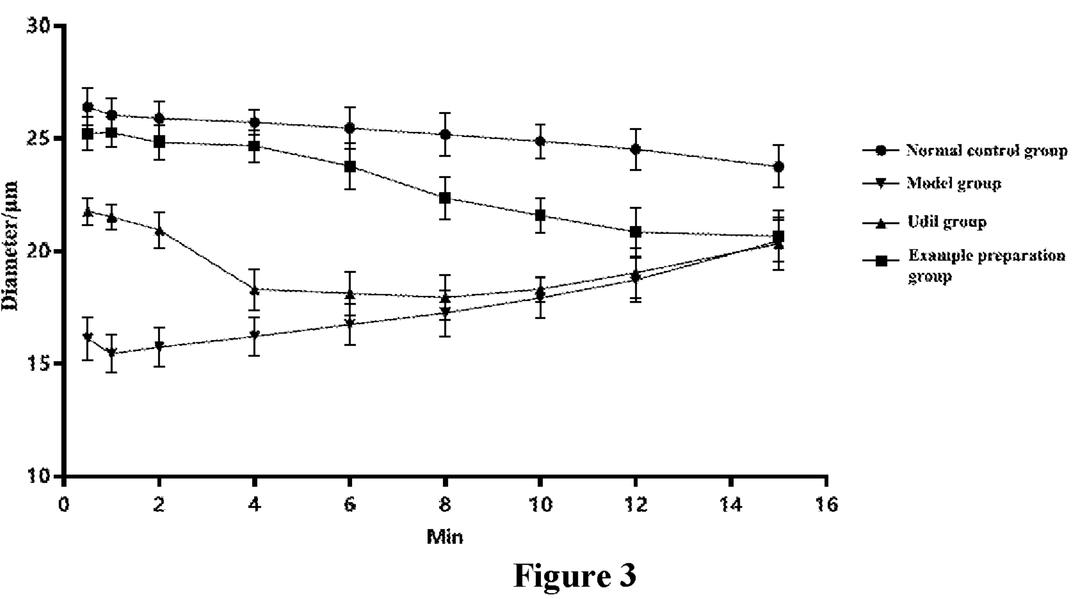
FIG. 3 is a curve showing the relationship between the diameter of the mesenteric arterioles and the administration time in Experimental Example 3.

As shown in FIG. 3, by measuring the diameter, the preparation group of Example 3 can significantly improve the microcirculation disorder caused by epinephrine, and there were significant differences between the preparation group of Example 3 and the model group from 0.5 to 10 minutes after administration ($P<0.05$). Compared with the model control group, the Udil group had no significant difference ($P>0.05$) at 4 min. The efficiency of improving microcirculation disorder caused by epinephrine in the Example group was significantly higher than that of Udil, and there was a significant difference between the two at 0.5-10 min ($P<0.05$).

Experimental Example 4

Determination of Free Drug in the Preparation

Sample processing method: the lyophilized emulsion of each Example was added with 10 ml for reconstitution, and one part was simultaneously diluted 10 times with water, and an appropriate amount was accurately metered and placed in a 20 ml brown test tube with a stopper. 2.5 ml of tetrahydrofuran was added, mixed well, and 15 ml of phosphoric acid solution (1→1000) was added, mixed well and passed through the pretreatment column [the filler was ODS with a particle size of 70 μm, ϕ10 mm×9 mm polypropylene tube (SEP-PAK C18 column, Waters), rinsed with 10 ml of methanol and 10 ml of water before use]. The test tube was rinsed with 10 ml of water and passed through the pretreatment column. Then 7 ml methanol was used for elution, and all the eluate was transferred into a 10 ml brown distillation flask and distilled under reduced pressure at 50° C. for 10 minutes. The solvent was evaporated, and the residue was dissolved with 1 ml internal standard solution and shaken well to obtain the sample.

The ODS was used as a filler, 0.0067 mol/L phosphate buffer (pH=6.3) (9.07 g of potassium dihydrogen phosphate was taken, and water was added to dissolve it to make 1000 ml solution; 9.46 g of anhydrous disodium hydrogen phosphate was separately taken, and water was added to dissolve it to make 1000 ml solution; the latter was added to the former until the pH was 6.3, 100 ml of this solution was taken and water was added to reach 1000 ml, and shaken well to get the buffer)-acetonitrile (70:30) was used as a mobile phase. The flow rate was 1 ml per minute; the post-column reaction solution was 1 mol·L−1 KOH solution, and the post-column reaction tube was a polytetrafluoroethylene tube (φ0.5 mm×10 m); column temperature was 60° C.; detection wavelength was 278 nm. 20 μl of each test substance and reference substance solution were injected, and calculated according to the internal standard peak area method.

Examples 3 to 18 and Udil were reconstituted with physiological saline to reach a concentration of 1 μg/mL, and all samples were diluted 10 times to 0.1 μg/mL, and appropriate amounts of the above-mentioned reconstituted preparations were taken and placed in an ultrafiltration centrifuge tube. After centrifugal ultrafiltration at 2800 rpm for 30 minutes, 1 ml of the filtrate was taken to prepare a sample solution according to the above sample processing method, and 20 μl of sample was injected. The measured content of each drug is the free drug content.

Meanwhile, the free rates of 1 mL of reconstituted emulsion (lx) and 10-fold dilution (lox) of the samples of each Example were measured.

$$\text{Free rate }\% = \text{total amount of free drug}/\text{total drug amount} \times 100\%$$

The measured free rate of each example is shown in Table 1 below:

TABLE 1

| Sample | Free rate (%) | |
|---|---|---|
| | 1 × (1 μg/ml) | 10 × (0.1 μg/ml) |
| Udil | 2.98 | 11.25 |
| Example 3 | 0.21 | 0.86 |
| Example 4 | 0 | 0 |
| Example 5 | 0.47 | 0.55 |
| Example 6 | 0.19 | 0.22 |
| Example 7 | 0.12 | 0.18 |
| Example 8 | 0.09 | 0.11 |
| Example 9 | 0.31 | 0.29 |
| Example 10 | 0.36 | 0.27 |
| Example 11 | 0.28 | 0.35 |
| Example 12 | 0.29 | 0.27 |
| Example 13 | 0.15 | 0.19 |
| Example 14 | 0.25 | 0.29 |
| Example 15 | 0.28 | 0.41 |
| Example 16 | 0.26 | 0.33 |
| Example 17 | 0.39 | 0.34 |
| Example 18 | 0.37 | 0.47 |

The experimental results show that the free drug of Examples 3-18 was significantly lower than that of Udil after reconstitution. When Udil was diluted by 10 times according to the instructions, the free rate increased significantly. However, there was no significant increase in the free drug of the preparations prepared in the Examples of the disclosure.

Experimental Example 5

Vascular Irritation Test

Twenty New Zealand white rabbits were selected and divided into 2 groups with a weight of about 2 kg. Both the preparations of the Examples and Udil were reconstituted with physiological saline to reach 1 μg/ml, and further diluted with physiological saline to 0.1 μg/ml. According to the clinical dosage of prostaglandin E1, 0.5 μg/kg was instilled slowly in the ear vein, and the same volume of physiological saline was injected in the ear vein at the opposite side, once a day for 7 days. Two hours after the last administration, the degree of vascular irritation was visually evaluated. All animals were sacrificed, and then the injection site was taken for histopathological examination. The results are shown in Table 2 and Table 3 below.

TABLE 2

General checklist of vascular irritation test

| Lesion area | Score |
|---|---|
| No obvious reaction | 0 |
| Mild hyperemia | 1 |
| Mild to moderate hyperemia, swelling | 2 |
| Mild to moderate hyperemia, swelling, drooping ears | 3 |
| Mild to moderate hyperemia, swelling, drooping ears with mild to moderate necrosis | 4 |
| Mild to moderate hyperemia, swelling, drooping ears with severe extensive necrosis | 5 |

The results showed that the Example group was substantially non-irritative ($P>0.05$), while the Udil group had obvious vascular irritation ($P<0.05$).

TABLE 3

| Group | | Vascular irritation score (Mean ± SD) |
|---|---|---|
| Preparation of Example | Administered ear | 0.40 ± 0.52 |
| | Control ear | 0 |
| Udil | Administered ear | 2.6 ± 0.84*# |
| | Control ear | 0 |

*P < 0.05 compared with the control ears in this group;
#P < 0.05 compared with the administered ears in the Example group Experimental Example 6

Preparation Stability Test

The appearance and particle size of the samples prepared in Examples 3 to 18 and Comparative Examples 1 and 2 are shown in Table 4 below:

TABLE 4

| | Appearance | Average particle size of the final product (nm) | >5 μm droplets (%) |
|---|---|---|---|
| Example 3 | Loose lumps, good reconstitution | 94 | 0.0021 |
| Example 4 | Loose lumps, good reconstitution | 93 | 0.0019 |
| Example 5 | Loose lumps, good reconstitution | 96 | 0.0022 |
| Example 6 | Loose lumps, good reconstitution | 77 | 0.0018 |
| Example 7 | Loose lumps, good reconstitution | 89 | 0.0019 |
| Example 8 | Loose lumps, good reconstitution | 148 | 0.0053 |
| Example 9 | Loose lumps, good reconstitution | 93 | 0.0037 |
| Example 10 | Loose lumps, good reconstitution | 104 | 0.0018 |
| Example 11 | Loose lumps, good reconstitution | 86 | 0.0025 |
| Example 12 | Loose lumps, good reconstitution | 86 | 0.0022 |
| Example 13 | Loose lumps, good reconstitution | 101 | 0.0019 |
| Example 14 | Loose lumps, good reconstitution | 113 | 0.0033 |
| Example 15 | Loose lumps, good reconstitution | 92 | 0.0024 |
| Example 16 | Loose lumps, good reconstitution | 99 | 0.0018 |
| Example 17 | Loose lumps, good reconstitution | 91 | 0.0038 |
| Example 18 | Loose lumps, good reconstitution | 89 | 0.0023 |
| Comparative Example 1 | White homogeneous milky liquid | 206 | 0.2502 |
| Comparative Example 2 | Unable to shaped | / | / |

380ZLS particle size analyzer (dynamic light scattering method) from PSS corporation was used to determine the average particle size, and the Accusizer 780 instrument (light blockage method) from PSS corporation was used to determine the large-size emulsion droplets, and the percentage of emulsion droplets larger than 5 μm was calculated. The results showed that the samples prepared in Examples 3-18 had a good appearance after lyophilization, an average particle size after reconstitution significantly smaller than that of Comparative Example 1, and a percentage of large emulsion droplets (>5 μm) much less than 0.05%, while the large particle size (>5 μm) of Comparative Example 1 exceeds the standard (>0.05%, USP standard), and Comparative Example 2 cannot be lyophilized.

The samples prepared in Examples 3, 5, 8, and 15 were taken for a 24-month long-term stability test (temperature 25° C.±2° C., humidity 60%±10%). The results are shown in Table 5 below:

TABLE 5

| | Storage time | Characters | Average particle size (nm) | drug content % |
|---|---|---|---|---|
| Example 3 | 0 month | Good appearance, normal reconstitution | 92 | 103.2% |
| | 3 months | Good appearance, normal reconstitution | 94 | 103.3% |
| | 6 months | Good appearance, normal reconstitution | 95 | 103.0% |
| | 9 months | Good appearance, normal reconstitution | 94 | 102.8% |
| | 12 months | Good appearance, normal reconstitution | 96 | 102.6% |
| | 18 months | Good appearance, normal reconstitution | 95 | 102.7% |
| | 24 months | Good appearance, normal reconstitution | 97 | 102.4% |
| Example 5 | 0 month | Good appearance, normal reconstitution | 88 | 101.5% |
| | 3 months | Good appearance, normal reconstitution | 87 | 101.3% |
| | 6 months | Good appearance, normal reconstitution | 93 | 101.4% |
| | 9 months | Good appearance, normal reconstitution | 91 | 101.1% |
| | 12 months | Good appearance, normal reconstitution | 93 | 100.8% |
| | 18 months | Good appearance, normal reconstitution | 95 | 100.4% |
| | 24 months | Good appearance, normal reconstitution | 94 | 100.4% |
| Example 8 | 0 month | Good appearance, normal reconstitution | 136 | 104.3% |
| | 3 months | Good appearance, normal reconstitution | 135 | 104.0% |
| | 6 months | Good appearance, normal reconstitution | 141 | 104.0% |
| | 9 months | Good appearance, normal reconstitution | 139 | 103.8% |
| | 12 months | Good appearance, normal reconstitution | 145 | 103.9% |
| | 18 months | Good appearance, normal reconstitution | 152 | 103.5% |
| | 24 months | Good appearance, normal reconstitution | 147 | 103.4% |
| Example 15 | 0 month | Good appearance, normal reconstitution | 93 | 102.5% |
| | 3 months | Good appearance, normal reconstitution | 95 | 102.5% |
| | 6 months | Good appearance, normal reconstitution | 94 | 102.1% |
| | 9 months | Good appearance, normal reconstitution | 99 | 102.2% |
| | 12 months | Good appearance, normal reconstitution | 97 | 101.5% |
| | 18 months | Good appearance, normal reconstitution | 103 | 101.7% |
| | 24 months | Good appearance, normal reconstitution | 103 | 101.4% |

The results showed that the lyophilized preparations of prostaglandin E1 methyl ester prepared in the Examples of the disclosure had stable product quality in the 24-month long-term stability test.

Experimental Example 7

Pharmacokinetic Study of Examples 3, 6, 7, 8 and Comparative Example 1 in Rats

Figure 4:
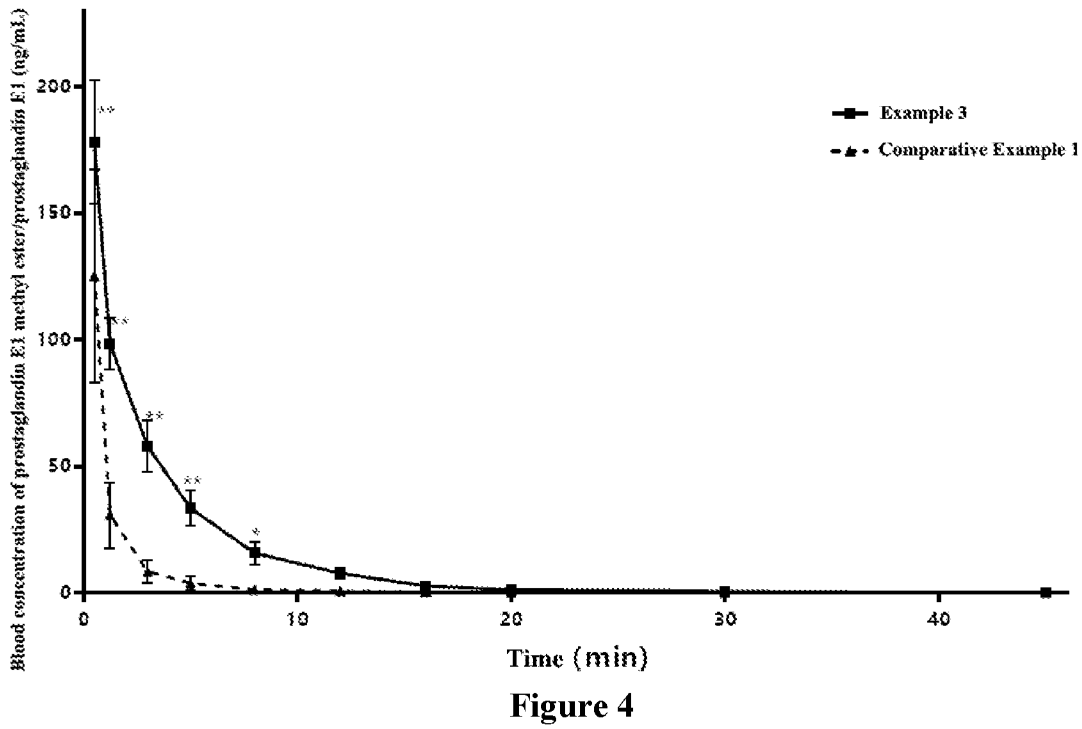
FIG. 4 is the plasma concentration-time curve of alprostadil after intravenous injection of 40 μg/kg alprostadil in rats.

In the pharmacokinetic experiment, 12 male SD rats were used in each group, fasted for 12 hours before administration, and given free drinking water. The two preparations were administered intravenously at a dose of 40 μg/kg respectively, and blood was collected from the orbit at 0.5 min, 1.25 min, 3 min, 5 min, 8 min, 12 min, 16 min, 20 min, 30 min, and 45 min after administration. The blood concentration (the sum of prostaglandin E1 methyl ester and prostaglandin) measured at each time point is shown in FIG. 4.

The pharmacokinetic parameters of the two preparations were calculated according to the blood concentration curve, the peak blood concentration after administration of Example 3 was significantly higher than that of Comparative Example 1, the half-life was significantly prolonged, and the bioavailability was also significantly improved (see Table 6).

TABLE 6

The pharmacokinetic parameters of 40 μg/kg intravenous injection of the preparations of Examples 3, 6-8 and Comparative Example 1 in rats

| | Cmax (ng/mL) | AUC(0-t) (ng/mL*min) | t½(min) |
|---|---|---|---|
| Example 3 | 178.1 ± 24.5 | 606.1 ± 100.4 | 6.6 ± 1.3 |
| Example 6 | 165.3 ± 31.8 | 671.1 ± 110.9 | 6.2 ± 0.9 |
| Example 7 | 168.5 ± 26.9 | 625.3 ± 82.4 | 7.1 ± 1.6 |
| Example 8 | 151.6 ± 24.6 | 591.6 ± 68.2 | 6.7 ± 1.1 |
| Comparative Example 1 | 125.3 ± 41.9 | 233.3 ± 78.8 | 2.3 ± 0.3 |

Compared with the preparation of Comparative Example 1, the preparations of Examples 3 and 6-8 have an obvious improvement in the pharmacokinetic behavior in vivo. This may be due to the inhibition of the metabolic inactivation of the drug in the pulmonary circulation, and this phenomenon may be related to the particle size of the drug.

The invention claimed is:

1. A method for producing a lyophilized preparation of prostaglandin E1 methyl ester for injection, wherein the method includes producing the lyophilized preparation with the following components as raw materials in weight percentage: 0.0001-0.01% of prostaglandin E1 methyl ester, 0.5-4% of an oil for injection, 0.5-1.5% of an emulsifier, 0-0.01% of a co-emulsifier, 5-50% of a lyoprotectant, 0.2-1.5% of glycerin, pH adjuster, and a balance of water for injection; the amount of the pH adjusting agent is such that the pH of the mixed solution is adjusted to 4.5-6.5 when the mixed solution is made up to the full volume with water for injection; the emulsifier is lecithin; the oil for injection is selected from one or more of soybean oil, olive oil, tea oil, corn oil, or castor oil; the co-emulsifier is selected from one or more of oleic acid, palmitic acid, stearic acid, linolenic acid, linoleic acid, and sodium oleate; the lyoprotectant is selected from one or more of lactose, sucrose, trehalose, mannitol, glucose, and maltose;

The method includes the following steps:

a. dispersing prostaglandin E1 methyl ester and ⅓ of the emulsifier uniformly in an oily solvent as an oil phase;

b. dissolving glycerin and the lyoprotectant and the remaining emulsifier in water for injection as a water phase, and adjusting the pH of the water phase to 4.5-6.5 with a pH regulator;

c. dissolving the co-emulsifier in the oil or water phase;

d. adding the oil phase to the water phase under stirring, or adding the water phase to the oil phase under stirring, and obtaining an initial emulsion by shearing, then diluting to full volume with water for injection;

e. homogenizing the initial emulsion to obtain a uniform emulsion; and f. sterilizing the obtained emulsion by filtration, packing, lyophilizing, and sealing to obtain the lyophilized preparation, wherein the lyophilizing includes pre-freezing at −50° C. to −35° C. for 100-200 minutes, and then vacuuming at 70-90 mTorr for 420-540 minutes at −25° C. to −15° C., then vacuuming at 50-70 mTorr for 240-360 minutes at 5° C. to 15° C., and then vacuuming at 35-45 mTorr for 300-420 minutes at 35° C. to 45° C., wherein the average particle size after lyophilizing is less than 100 nm and greater than or equal to about 77 nm; and wherein the lyophilized preparation comprises the following components as raw materials by weight: 0.1-10 parts of prostaglandin E1 methyl ester, 500-4000 parts of soybean oil, 500-1500 parts of lecithin, 0-10 parts of sodium oleate, 5000-20000 parts of lactose, 20-1500 parts of glycerin, an appropriate amount of sodium citrate or hydrochloric acid, and a balance of water for injection based on $100\times10^3$ parts of the total weight of raw materials.

2. The method according to claim 1, wherein step d comprises shearing at a constant temperature of 20° C.-50° C.

3. A lyophilized preparation of prostaglandin E1 methyl ester for injection, wherein the lyophilized preparation is prepared by the method of claim 1.

* * * * *